United States Patent
Zobele (10) Patent No.: US 6,996,335 B2
(45) Date of Patent: *Feb. 7, 2006

(54) ELECTRICAL EVAPORATOR WITH RATCHETING WICK ADJUSTER

(75) Inventor: Franco Zobele, Trento (IT)

(73) Assignee: S.C. Johnson & Son, Inc., Racine, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 10/776,160

(22) Filed: Feb. 12, 2004

(65) Prior Publication Data

US 2005/0180736 A1    Aug. 18, 2005

(51) Int. Cl.
*F24F 6/08*    (2006.01)

(52) U.S. Cl. ...................................... 392/395; 392/386
(58) Field of Classification Search ......... 392/386–395
See application file for complete search history.

(56) References Cited

U.S. PATENT DOCUMENTS

| | | | |
|---|---|---|---|
| 2,472,992 A | 6/1949 | Szekely | 21/117 |
| 3,872,280 A | 3/1975 | Van Dalen | 219/271 |
| 4,968,487 A | 11/1990 | Yamamoto et al. | 422/125 |
| 5,038,394 A | 8/1991 | Hasegawa et al. | 392/395 |
| 5,095,647 A | 3/1992 | Zobele et al. | 43/125 |
| 5,114,625 A | 5/1992 | Gibson | 261/30 |
| 5,222,186 A | 6/1993 | Schimanski et al. | 392/395 |
| 5,290,546 A | 3/1994 | Hasegawa et al. | 424/76.2 |

(Continued)

FOREIGN PATENT DOCUMENTS

EP    0943344 A1    9/1999

(Continued)

OTHER PUBLICATIONS

Four sheets of drawings of a Three-Position Adjuster, 2001, pp. 1-4.

*Primary Examiner*—Thor S. Campbell (57) ABSTRACT

An evaporator (10) includes a housing (100, 200), a bottle (400) containing a substance to be evaporated, a wick (500) protruding from the bottle (400), a rotatable plug deck (300) for providing electricity to the evaporator (10), a heating device (250) disposed within the housing (100,200), and an adjuster (600) within the housing (100, 200) for displacing the wick (500) toward or away from the heating device (250). The adjuster (600) includes a retaining mechanism (650) that retains the adjuster (600) in a selected one of a plurality of discreet adjustment settings. The plug deck 300 includes a locking mechanism (340, 342) that retains the plug deck (300) in a selected one of a plurality of discrete positions.

19 Claims, 9 Drawing Sheets

U.S. PATENT DOCUMENTS

| | | | | |
|---|---|---|---|---|
| 5,402,517 A | 3/1995 | Gillett et al. | ............... | 392/386 |
| 5,647,053 A | 7/1997 | Schroeder et al. | ........... | 392/390 |
| 5,909,845 A | 6/1999 | Greatbatch et al. | ............ | 239/44 |
| 6,078,728 A * | 6/2000 | O'Rourke et al. | ........... | 392/390 |
| 6,104,867 A | 8/2000 | Stathakis et al. | ........... | 392/403 |
| 6,145,241 A | 11/2000 | Okuno | ........................ | 43/129 |
| 6,278,840 B1 | 8/2001 | Basagañas Millan | ....... | 392/390 |
| 6,285,830 B1 | 9/2001 | Basaganas Millan | ....... | 392/395 |
| 6,361,752 B1 | 3/2002 | Demarest et al. | ........... | 422/306 |
| 6,446,583 B2 | 9/2002 | Vieira | ........................ | 122/366 |
| 6,466,739 B2 | 10/2002 | Ambrosi et al. | ............ | 392/395 |
| 6,567,613 B2 | 5/2003 | Rymer | ........................ | 392/390 |
| 6,580,875 B2 | 6/2003 | Rymer | ........................ | 392/395 |
| 6,782,194 B2 * | 8/2004 | Schneiderbauer | ........... | 392/395 |
| 2002/0021892 A1 | 2/2002 | Ambrosi et al. | ............ | 392/395 |
| 2003/0007787 A1 | 1/2003 | Rymer | ........................ | 392/395 |
| 2003/0138241 A1 * | 7/2003 | Pedrotti et al. | ............. | 392/395 |
| 2003/0152375 A1 | 8/2003 | Schneiderbauer | ........... | 392/395 |
| 2004/0021001 A1 | 2/2004 | Zobele | ........................ | 239/44 |

FOREIGN PATENT DOCUMENTS

| | | |
|---|---|---|
| EP | 0962132 A1 | 12/1999 |
| EP | 1175833 A1 | 1/2002 |
| ES | 1 005 422 | 11/1988 |
| WO | WO 98/19526 | 5/1998 |
| WO | WO 03/061716 A1 | 7/2003 |

* cited by examiner

ELECTRICAL EVAPORATOR WITH RATCHETING WICK ADJUSTER

FIELD OF THE INVENTION

The invention relates generally to an electrical evaporator for use with liquid formulations containing a chemical active such as an insecticide, a fragrance, an odor eliminator, or the like, and, in particular, to an electrical evaporator having an adjustable intensity feature that enables variation of the evaporation rate of the liquid formulation between a minimum and maximum level.

BACKGROUND OF THE INVENTION

Electrical evaporators in which the evaporation rate of a liquid formulation from a wick can be adjusted by varying the relative positions of a heating device and the wick are known.

For example, Spanish Utility Model No. 1 005 422 discloses an evaporator in which a heating device and a wick can be moved vertically relative to one another by means of a mechanical device, such as a screw/nut thread mechanism, in order to increase or decrease the heat intensity to which the wick is exposed. European Patent Publication No. 0 942 648, by contrast, discloses an evaporator in which a heating device remains stationary while a wick and bottle are displaced vertically in the direction of the longitudinal axis of the wick using a screw/nut thread mechanism, thereby increasing or reducing the overlap between the wick and the heating device. Another type of evaporator is disclosed in European Patent Publication No. 0 943 344. In that evaporator, a heating device is mounted on a plug, which can be moved toward or away from a wick. U.S. Patent Application Publication No. 2003/0138241 A1 ("the '241 publication"), which is incorporated herein by reference, discloses yet another type of evaporator having an adjuster for displacing the upper portion of a wick toward or away from a heating device in a direction substantially perpendicular to the longitudinal axis of the wick. Several perceived shortcomings of these adjustable evaporators are that they are difficult to adjust in discrete intervals and that repeatability of adjustment is difficult.

In addition, some types of plug-in appliances, particularly wick-based evaporators, must be used in an upright orientation in order to work properly. Because some electrical outlets are vertical (i.e., one socket is above another one), while other outlets are horizontal (i.e., side-by-side sockets), it is preferable for these appliances to have a rotatable plug, which permits the device to be used in both vertical and horizontal outlets. U.S. Pat. No. 5,647,053, which also is incorporated by reference herein, discloses a wick-based evaporator having a rotatable plug. One perceived shortcoming of the forgoing type of evaporator is that it is difficult to tell when the plug is in a proper position for use. Also, the forgoing evaporators have no provision for locking the plug in the use-positions.

SUMMARY OF THE INVENTION

My invention remedies these and other deficiencies in the prior art and provides an electrical evaporator having an improved adjuster for quickly and easily varying the evaporation rate of the liquid formulation, and an improved rotatable plug assembly.

In one aspect, my invention relates to an evaporator comprising a housing adapted to receive a bottle with a wick protruding therefrom, an electrical plug assembly coupled to the housing for supporting the evaporator in a wall outlet, a heating device disposed within the housing in electrical communication with the electrical plug assembly, and an adjuster. The adjuster is disposed within the housing and is adapted to adjust a spacing of the wick relative to the heating device. The adjuster includes a retaining mechanism that retains the adjuster in one of a plurality of discreet adjustment settings.

In another aspect, my invention relates to an evaporator comprising a housing adapted to receive a bottle with a wick protruding therefrom, a heating device disposed within the housing and adapted apply heat to the wick, and an electrical plug assembly. The electrical plug assembly includes a plug deck and is coupled to the housing for supporting the evaporator in a wall outlet and supplying power to the heating device. The plug deck is rotatable in order to support the evaporator in an upright position in both horizontal and vertical wall outlets. The plug deck includes a locking mechanism, which retains the plug deck in one of a plurality of discrete positions relative to the housing.

In still another aspect, my invention relates to an evaporator comprising a housing adapted to receive a bottle with a wick protruding therefrom, a heating device disposed within the housing and adapted to apply heat to the wick, an electrical plug assembly, and an adjuster. The electrical plug assembly includes a plug deck and is coupled to the housing for supporting the evaporator in a wall outlet and supplying power to the heating device. The plug deck is rotatable in order to support the evaporator in an upright position in both horizontal and vertical wall outlets. The plug deck includes a locking mechanism, which retains the plug deck in a selected one of a plurality of discrete positions relative to the housing. The adjuster is disposed within the housing and is adapted to adjust a spacing of the wick relative to the heating device. The adjuster includes a retaining mechanism that retains the adjuster in one of a plurality of discreet adjustment settings.

A better understanding of these and other features and advantages of the invention may be had by reference to the drawings and to the accompanying description, in which preferred embodiments of the invention are illustrated and described.

BRIEF DESCRIPTION OF THE DRAWINGS

Throughout the figures, like or corresponding reference numerals have been used for like or corresponding parts.

DESCRIPTION OF THE PREFERRED EMBODIMENTS

An evaporator 10 according to one preferred embodiment of my invention is illustrated in FIGS. 1–11.

Figure 1:
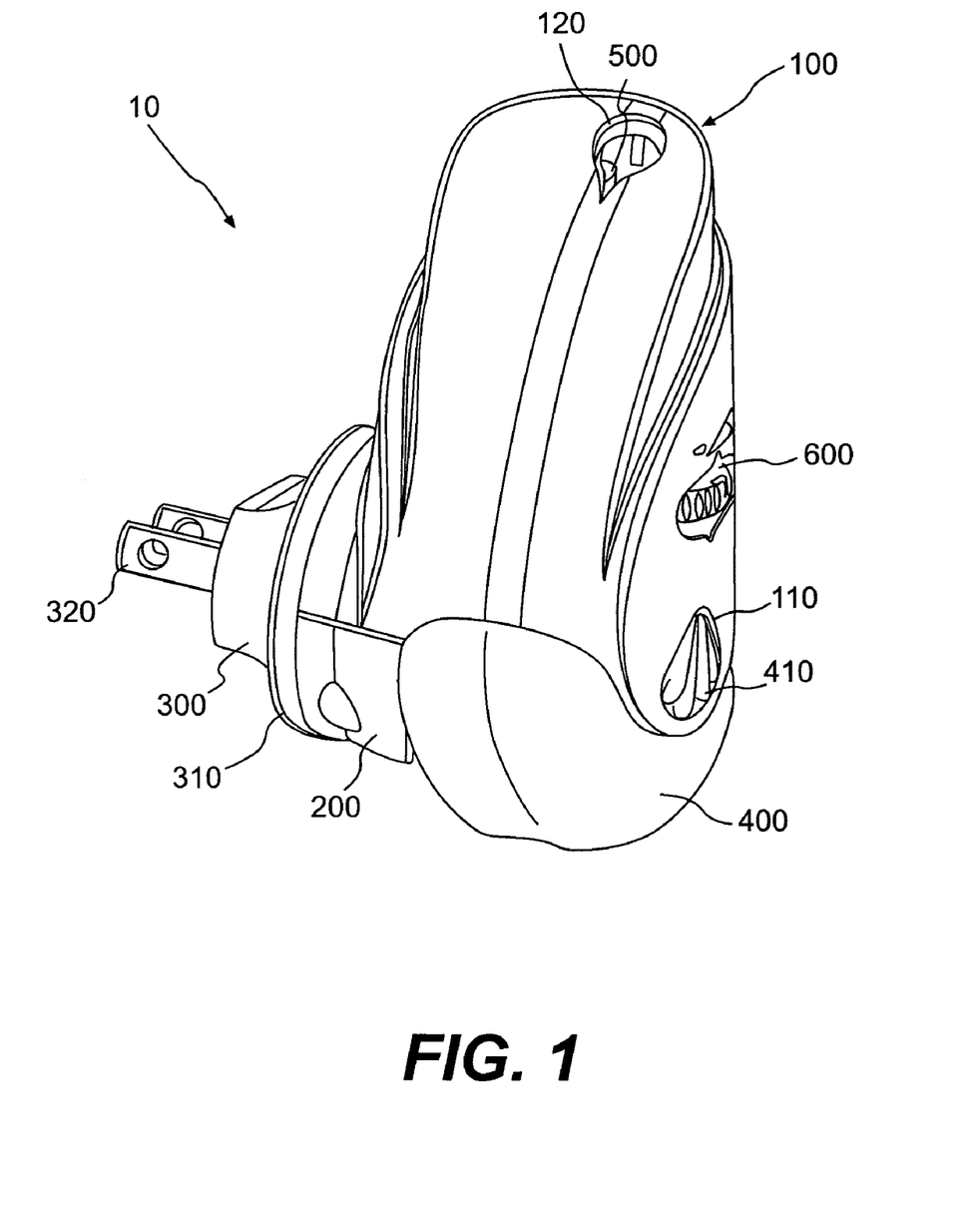
FIG. 1 is a perspective view of an evaporator according to a first preferred embodiment of my invention.

As shown in FIG. 1, the evaporator 10 comprises a multi-piece housing, including an upper housing 100 and a lower housing 200, in which a bottle 400 is detachably retained. The evaporator 10 further comprises an electrical plug assembly, including a plug deck 300, rotatably secured between the upper housing 100 and the lower housing 200. The bottle 400 contains an evaporable substance (not shown), such as, for example, a liquid formulation including a chemical active such as an insecticide, fragrance, odor eliminator, or the like. The term "bottle" is used herein in its broadest possible sense, including any receptacle, container, pouch, etc., capable of holding a liquid formulation. A raised pattern 410 on one side of the bottle is engaged by an opening 110 in a front surface of the upper housing 100 of the evaporator 10, in order to secure the bottle 400 within the evaporator 10. The front surface of the upper housing 100 is sufficiently pliant so that pulling the bottle 400 in a downward direction causes the raised pattern 410 to release from the opening 110 in the front surface of the upper housing 100, thereby enabling removal of the bottle 400 from the evaporator 10. Alternatively, a neck portion of the bottle may be designed to snap to, or screw into, the evaporator housing. Suitable refill bottles are available in a wide variety of liquid formulations from S.C. Johnson & Son, Inc., of Racine, Wis., under the GLADE® PLUGINS® and RAID® brand names.

Figure 2:
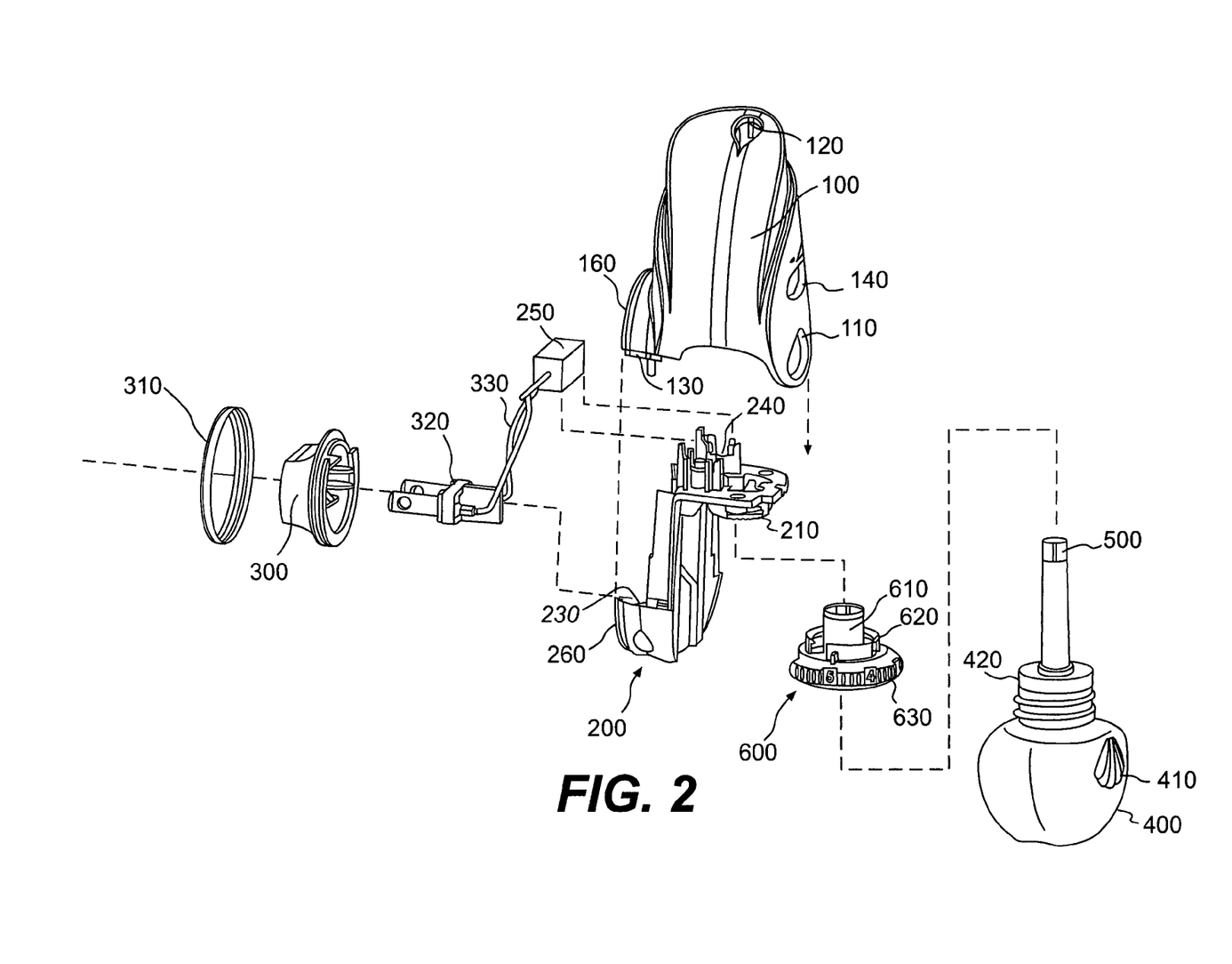
FIG. 2 is an exploded assembly view of the evaporator of FIG. 1.

As best shown in FIG. 2, a wick 500 is attached to the neck of the bottle 400 for drawing the liquid formulation out of the bottle 400 and toward an upper portion of the wick 500. A lower portion of the wick 500 is immersed in the liquid formulation, and the upper portion of the wick 500 protrudes above the neck of the bottle 400. Preferably, the wick 500 is positioned within the bottle 400 by a cap 420, which includes a sheath that encases the upper portion of the wick 500, except for an open area near the tip of the wick 500. Alternatively, a cap without a sheath can be utilized. Preferably, the wick 500 is about 7 mm in diameter and is constructed of ultra high molecular weight high-density polyethylene.

In the preferred embodiment illustrated in FIGS. 1–10, the evaporator multi-piece housing comprises an upper housing 100 and a lower housing 200, which are fastened together by heat-staking or any other suitable fastening means, including, for example, rivets, press fit, snap fit, screws, ultrasonic welding, adhesives, or the like. As best illustrated in FIG. 2, a lower back portion of the upper housing 100 forms an upper semicircular arch 160, the ends of which define an upper interface surface 130. The lower housing 200 has a corresponding inverted, semicircular arch 260, the ends of which define a lower interface surface 230. When the upper and lower housings 100, 200 are assembled, the upper and lower semicircular arches 160, 260 combine to form a ring that retains the plug deck 300. The plug deck 300 includes a groove about its circumference. When the upper and lower housings 100, 200, are assembled, the upper and lower semicircular arches 160, 260, fit into the groove in the circumference of the plug deck 300, such that the plug deck 300 is secured to the multi-piece housing in a manner that allows the plug deck 300 to rotate. The collar 310 fits over the ring formed by the upper and lower arches 160, 260, and helps to ensure that the upper and lower arches 160, 260, are held snugly together at the interface surfaces 130, 230. An electrical contact 320 protrudes through the plug deck 300 and serves the dual purpose of supplying power to the electrical components of the evaporator 10 and also supporting the evaporator 10 in a wall outlet (not shown). Preferably, the plug deck 300 is rotatable (as described in more detail below) in order to support the evaporator 10 in an upright position in both horizontal and vertical wall outlets. The electrical contact 320 is electrically connected via conventional electrical conductors 330, such as wires or electrodes, to a heating device 250 for applying heat to the wick 500, when the evaporator 10 is plugged into a wall socket. The heating device 250 is positioned adjacent to a window 120 in the upper housing 100, such that it faces the tip of the wick 500 when the bottle 400 is inserted in the evaporator 10. Heating the wick 500 enhances the rate at which the liquid formulation evaporates and is diffused through the window 120 and into the surrounding environment. Preferably, the heating device 250 is a 6 kΩ metal oxide resistor potted in a ceramic block, which is capable of handling up to at least about 5 Watts. The resistor preferably has PTC (positive temperature coefficient) characteristics, meaning that its resistance value increases slightly as the resistor heats up. A suitable resistor is available from Great Land Enterprise Co., Ltd., of Shenzhen, China, for example. Alternatively, the heating device 250 can comprise any other suitable type of heating device, such as a resistance heater, a wire-wound heater, a PTC heater, or the like.

The evaporator 10 also includes an adjuster 600 that positions the upper portion of the wick 500 in one of a plurality of discrete positions, relative to the heating device 250. Preferably, the adjuster 600 includes a hollow cylindrical portion 610 that surrounds and engages part of the upper portion of the wick 500. The adjuster 600 also includes a dial portion 630, accessible through an adjustment aperture 140 in the upper housing 100 (see, e.g., FIG. 3), for rotating the cylindrical portion 610 about an axis of rotation. The dial portion 630 preferably is formed integrally with the cylindrical portion 610, although it need not be.

Figure 6A:
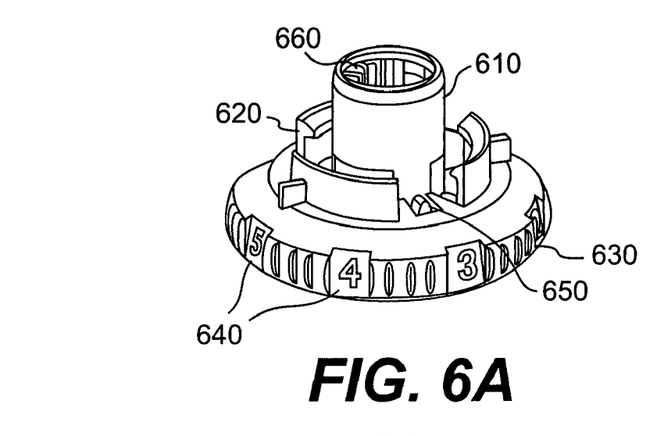
FIG. 6A is an elevated perspective view of the adjuster of FIG. 1.
Figure 6B:
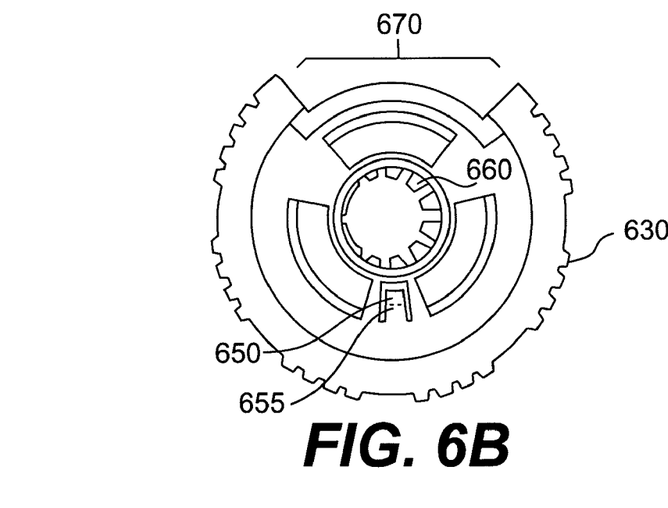
FIG. 6B is a bottom view of the adjuster of the evaporator of FIG. 1.

Preferably, as shown in FIGS. 6A and 6B, a plurality of tapered lugs 660 is provided on the inner surface of the cylindrical portion 610. The lugs 660 are widest at their uppermost point, where they come in contact with the wick 500, and narrowest near the bottom of the cylindrical portion 610. At their uppermost point, the lugs 660 define a circular opening that is just large enough for the wick 500 to fit through. The center of this opening is offset relative to the axis of rotation of the cylindrical portion 610, as best shown in FIG. 6B.

Figure 3:
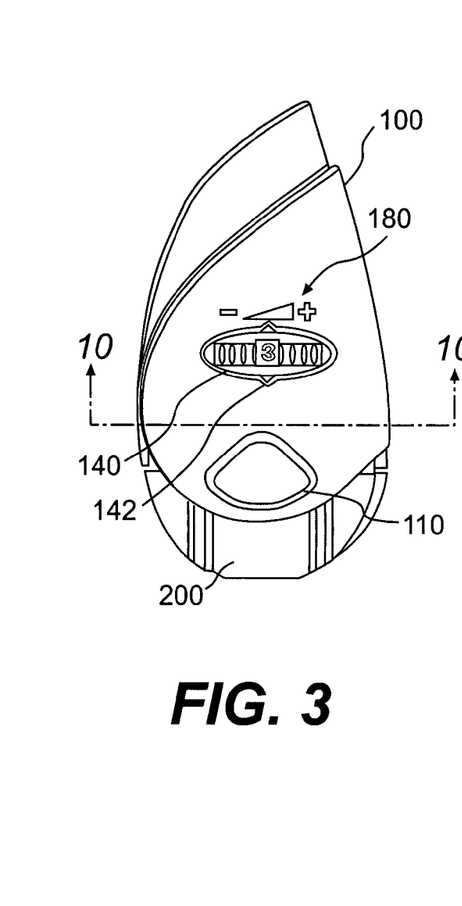
FIG. 3 is a front view of the evaporator of FIG. 1, set at an intermediate evaporation rate.

Setting indicators 640, from one to five, are formed around the exterior of the dial portion 630, to indicate to a user the current evaporation rate setting, with one being the lowest setting and five being the highest setting. The user can observe which of the setting indicators 640 is showing through the adjustment aperture 140 in the upper housing 100. A setting marker 142 formed on the upper housing 100 demarks the center of the adjustment aperture 140. In addition, an intensity scale or key 180 is positioned above the adjustment aperture 140 to indicate to the user which direction to rotate the dial portion 630 to increase (+) or decrease (−) the evaporation rate. For example, the evaporator 10 shown in FIG. 3 is in an intermediate evaporation rate setting, as evidenced by the number three setting indicator 640 being aligned with the setting marker 142. To increase the evaporation rate, the user has only to rotate the dial portion 630 toward the (+) symbol on the key 180 (i.e., to the right in FIG. 3). Conversely, to decrease the evaporation rate, the user simply rotates the dial portion 630 toward the (−) symbol (i.e., to the left in FIG. 3). While the indicators 640 are illustrated as being Arabic numerals, any other suitable indicators, such as roman numerals, symbols, colors, pictures, or the like, could also be used. Also, while five indicators are illustrated, any desired number of indicators could be used.

Figure 11:
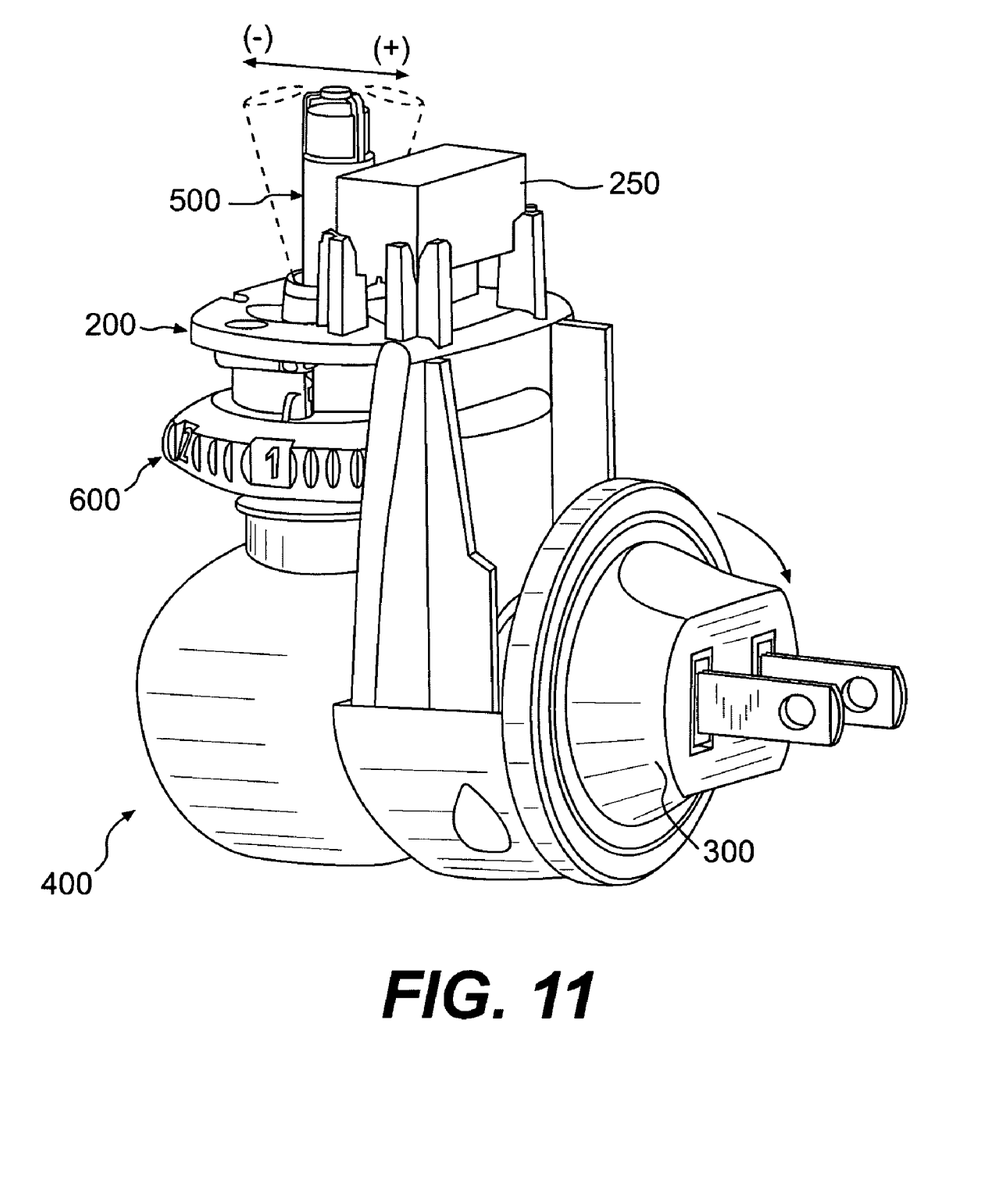
FIG. 11 is a perspective view of the evaporator of FIG. 1, with the upper housing removed for clarity. The movement of the wick is exaggerated in this view.

FIG. 11 illustrates the evaporator 10 in the same intermediate evaporation setting as FIG. 3. Rotating the dial portion 630 of the adjuster 600 causes the wick 500 to move toward (the (+) direction in FIG. 11) or away (the (−) direction in FIG. 11) from the heating device 250 in a lateral direction, i.e., in a direction substantially perpendicular to the longitudinal axis of the wick 500. The position of the wick 500 in minimum (−) and maximum (+) evaporation intensity settings is shown in phantom lines in FIG. 11. These minimum and maximum settings are exaggerated in FIG. 11 for clarity. In the minimum intensity setting, the axis of the wick 500 is positioned about 6.3 mm from the heating device 250. In this position, the wick is heated to a temperature of about 71–78 degrees Celsius. Rotating the dial portion 630 approximately 180 degrees to the right brings the wick axis to a position that is about 4.4 mm from the heating device 250. At this maximum setting, the wick is heated to a temperature of about 85–90 degrees Celsius, thereby resulting in a higher evaporation rate. The lateral distance traveled by the wick 500 in moving from the minimum intensity setting to the maximum intensity setting is preferably between about 1 mm and about 3.5 mm. In the particular preferred embodiment described above, the lateral distance traveled by the wick 500 is about 2 mm. Weight loss tests have demonstrated that the evaporation rate is almost 100 percent higher at the maximum setting than at the minimum setting.

The angle through which the dial portion 630 must be rotated to move the wick 500 through its full range of motion is not crucial and may be easily varied by, for example, adjusting the degree of eccentricity of the tapered lugs 660.

Figure 7:
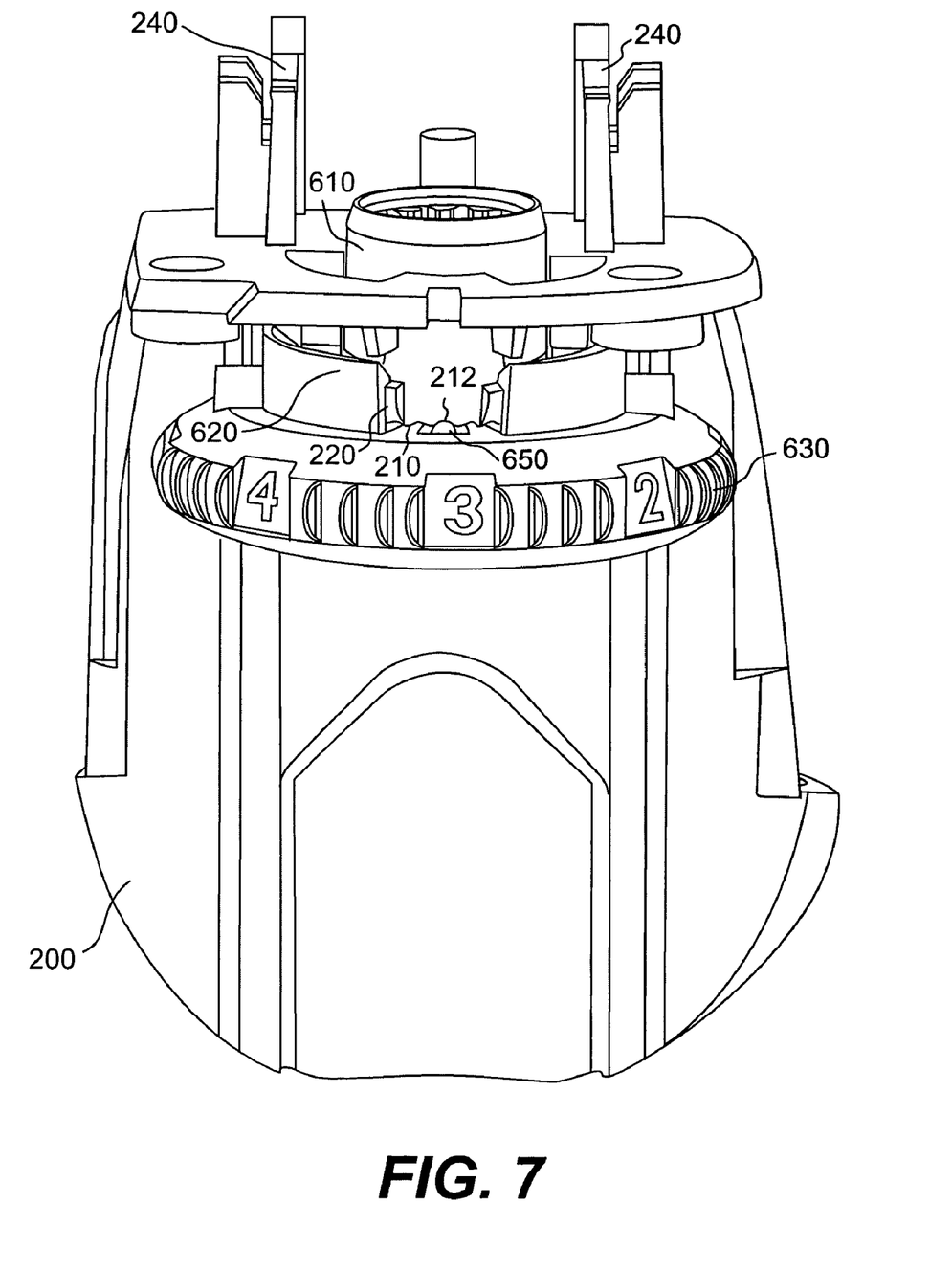
FIG. 7 is a front elevation view of the evaporator of FIG. 1, with the upper housing and wick removed for clarity.

The evaporator 10 also can be set to any one of a plurality of discrete intermediate settings between the minimum and maximum settings. The adjuster includes a retaining mechanism that retains the adjuster 600 in one of the plurality of these discrete adjustment settings. As shown in FIG. 7, the retaining mechanism of the adjuster 600 preferably comprises a rigid retaining dog 650 connected to the dial portion 630 of the adjuster 600 by a flexible, cantilever arm 655. The retaining dog 650 depends from the cantilever arm 655 and is biased by the cantilever arm 655 into contact with a serrated surface 210 of the lower housing 200. A retaining lip 620 of the adjuster 600 engages a flange 220 of the lower housing to hold the adjuster 600 and, consequently, the retaining dog 650, in contact with the serrated surface 210.

Figure 5:
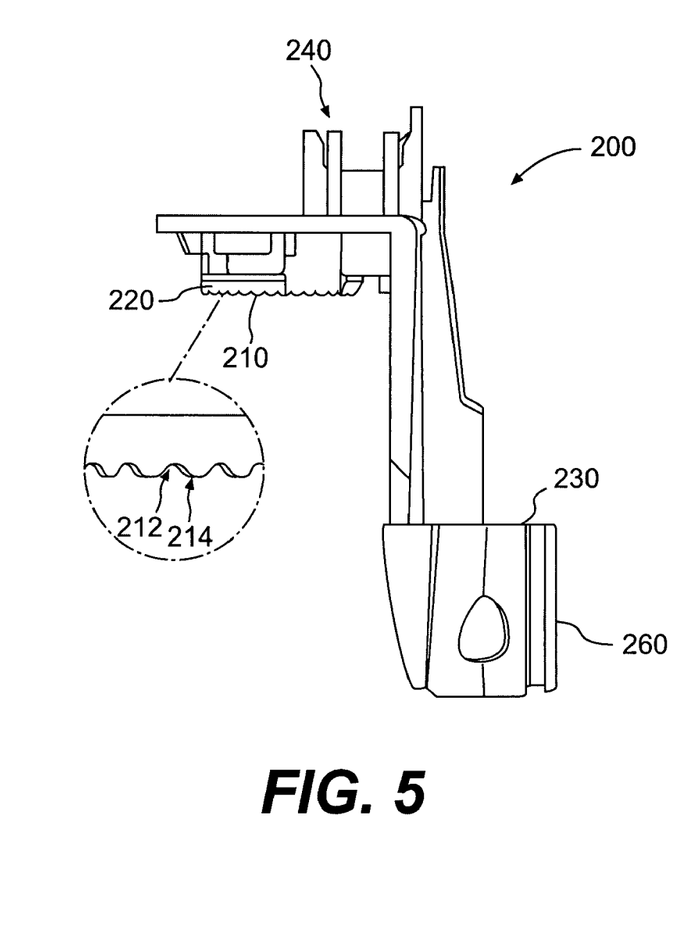
FIG. 5 is a side view of the lower housing of the evaporator of FIG. 1, with an enlarged detail of the serrated surface of the lower housing.

The serrated surface 210 of the lower housing comprises a plurality of peaks 214 and valleys 212 arranged in a substantially circular configuration, as best illustrated in the enlarged detail view of FIG. 5. Each of the valleys 212 corresponds to one of the plurality of discrete settings. Thus, as a user rotates the dial portion 630 of the adjuster 600, the retaining dog 650 rides along the serrated surface 210 and provides a ratcheting sound and feel, whereby the user can sense (by both auditory and tactile perception) the movement of the adjuster 600 from one discrete setting to the next as the retaining dog 650 rides up and over each successive peak 214 and down into the next successive valley 212.

The ratcheting action of the adjuster 600 makes it easier for the user to quickly adjust the evaporation rate of the evaporator 10 by a predetermined amount, for example, four valleys. Accordingly, repeatability of adjustment is also simplified, since the adjuster 600 can simply be adjusted through a known number of valleys, rather than trying to match the indicator with a previous setting.

Preferably, a cutout section 670 of the adjuster 600 limits the range of motion of the adjuster to approximately 75 degrees. Alternatively, however, the adjuster 600 could be made to rotate through any other desired angle, including being continuously rotatable.

Figure 8A:
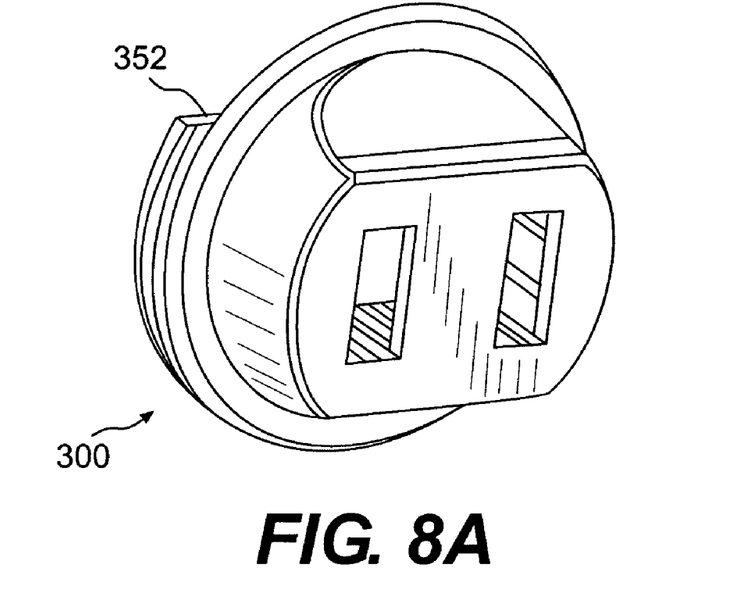
FIG. 8A is a perspective view of the front/outer surface of the plug deck of the evaporator of FIG. 1.
Figure 8B:
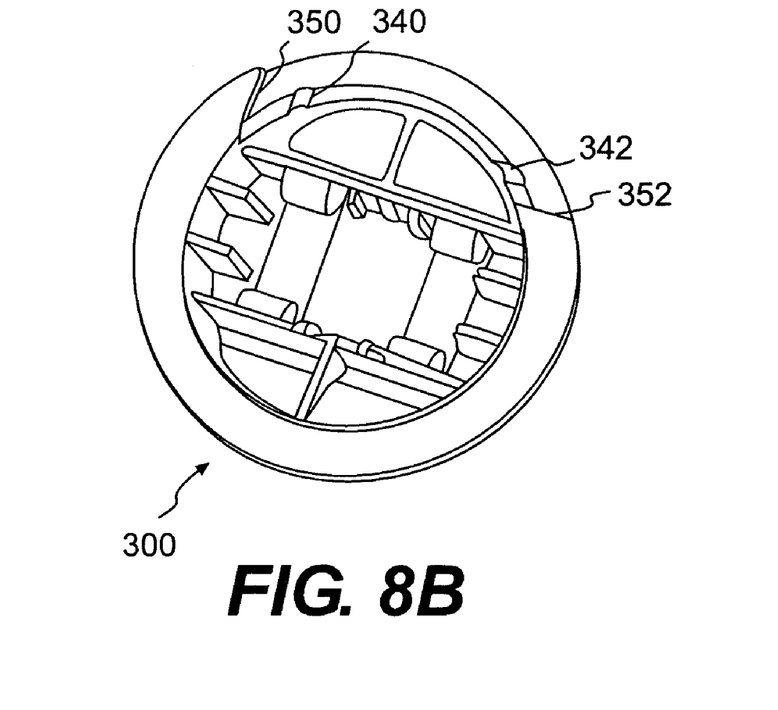
FIG. 8B is a perspective view of the back/inner surface of the plug deck of the evaporator of FIG. 1.
Figure 9:
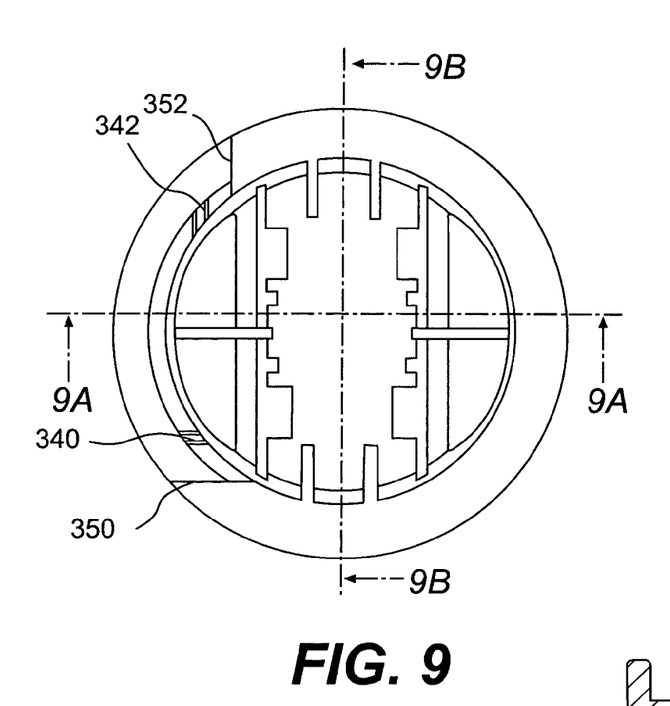
FIG. 9 is a back view of the plug deck of the evaporator of FIG. 1.
Figure 9A:
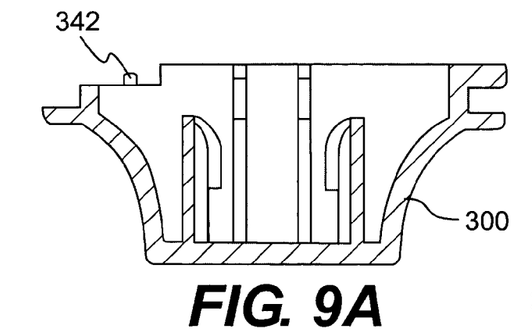
FIG. 9A is a cross-sectional view taken along line 9A—9A in FIG. 9.
Figure 9B:
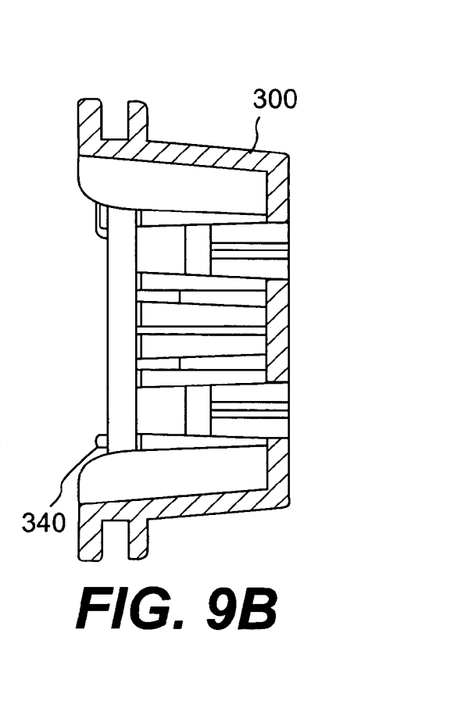
FIG. 9B is a cross-sectional view taken along line 9B—9B in FIG. 9.
Figure 10:
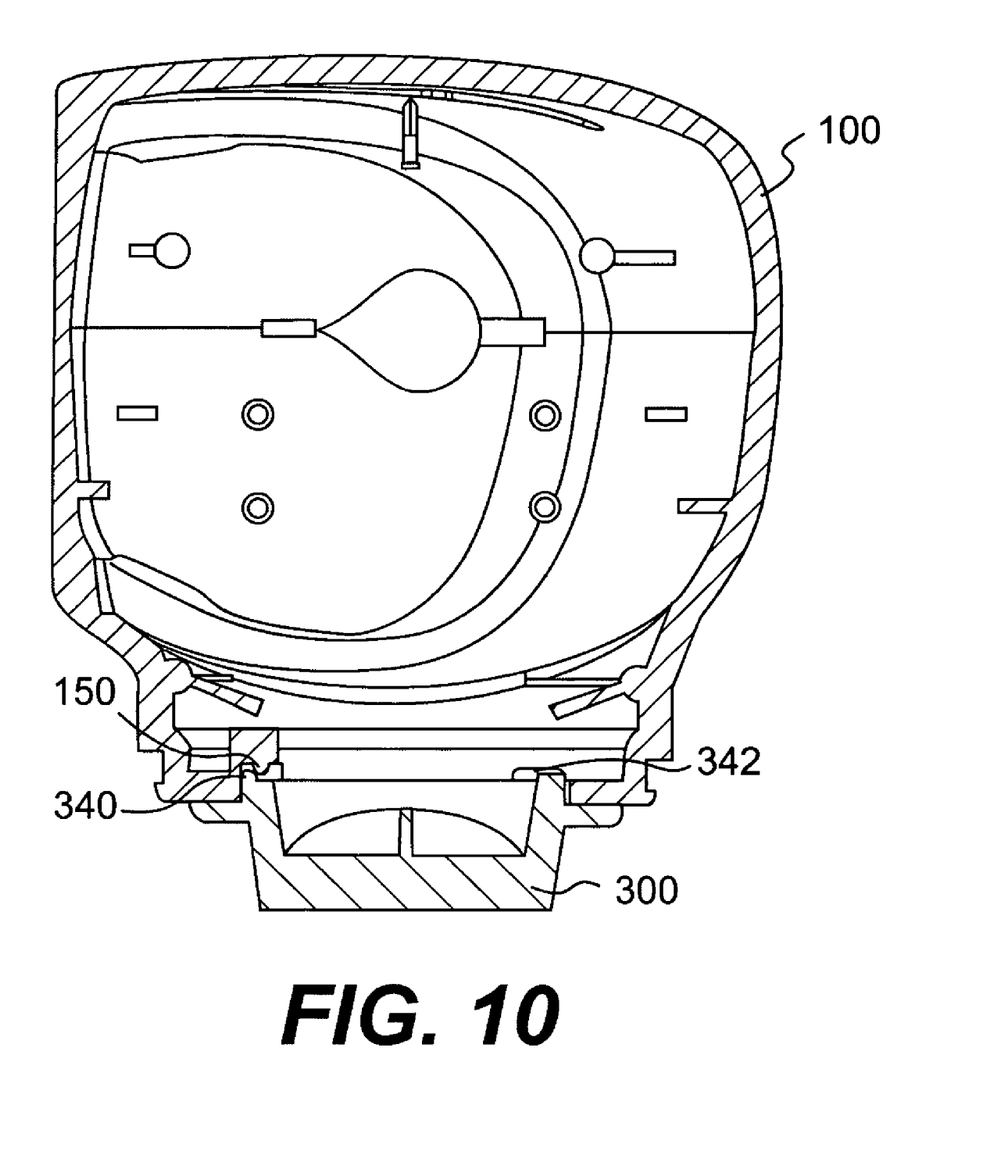
FIG. 10 is a cross-sectional view taken along line 10—10 in FIG. 3, illustrating the engagement of the housing with the plug deck of the evaporator of FIG. 1.

As mentioned above, the electrical plug assembly, including the plug deck 300, is preferably rotatable in order to support the evaporator 10 in an upright position in both horizontal and vertical wall outlets. The plug deck 300 is provided with a locking mechanism, which locks the plug deck 300 in the desired one of a plurality of use positions. As illustrated in FIGS. 8–10, the locking mechanism preferably comprises a stationary protrusion 150 formed on the upper housing 100 and a pair of left- and right-locking protrusions 340, 342 formed at different positions on the plug deck 300. The plug deck 300 preferably also includes a pair of left and right stop faces 350, 352 for limiting the rotation of the plug deck 300 to a desired range of angles. In the preferred embodiment shown in FIGS. 8–10, the plug deck 300 is rotatable through only about 90 degrees; however, it may be desirable in some instances to make the plug deck rotatable through any desired angle, such as 180 degrees, 360 degrees, or even continuously rotatable. While the preferred construction of the locking mechanism is described, those skilled in the art will understand that the locking mechanism may be constructed by any combination of protrusions and indentions, formed on either the housing 100, 200 or the plug deck 300, which allows the plug deck 300 to be locked in a plurality of different positions. Thus, another suitable configuration of the locking mechanism includes at least one of a protrusion and an indentation formed on the housing, which engages at least the other of a protrusion and an indentation formed on the plug deck.

Figure 4A:
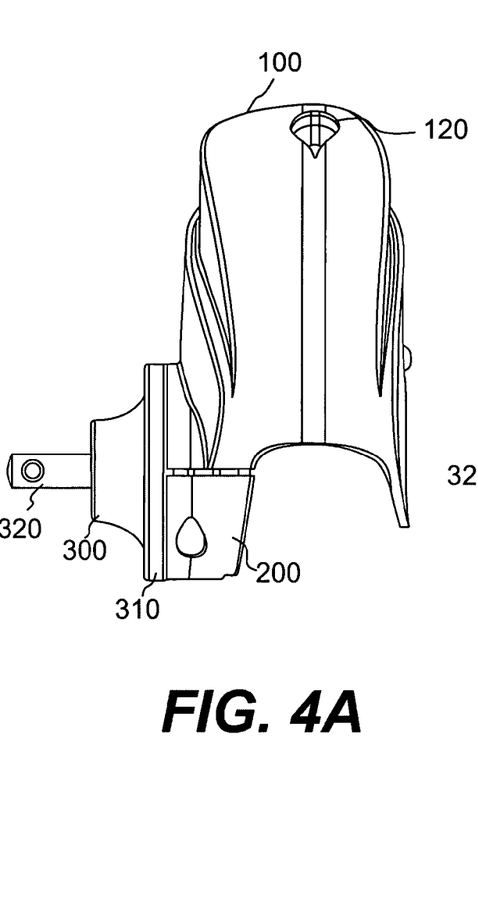
FIG. 4A is a left-side view of the evaporator of FIG. 1, with the plug deck set in a vertical socket mounting position.
Figure 4B:
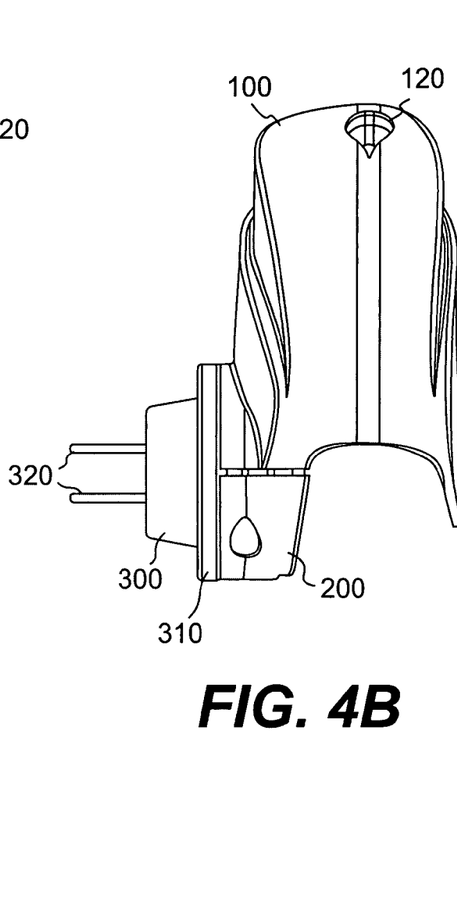
FIG. 4B is a left-side view of the evaporator of FIG. 1, with the plug deck in a horizontal socket mounting position.

The plug deck 300 is shown in FIGS. 4, 10, and 11, in a position for use in a vertical wall socket, with the plug deck 300 rotated in a maximum counter-clockwise direction. In this position, the left stop face 350 abuts with a portion of the upper housing 100 to prevent further rotation in the counter-clockwise direction, while the left-locking protrusion 340 is locked in place by the stationary protrusion 150. When the user desires to plug the evaporator 10 into a horizontal wall socket, the user simply rotates the plug deck 300 in the clockwise direction to the orientation shown in FIG. 4B. As the user begins to rotate the plug deck 300 in the clockwise direction, the left-locking protrusion 340 rides-up against the stationary protrusion 150, which causes the plug deck 300 to separate slightly from the upper housing 100 in the axial direction (downward in FIG. 10), as allowed by a slight deformation of the plug deck 300 and the upper housing 100. This slight separation allows the left-locking protrusion 340 to slip over the stationary protrusion 150. The plug deck 300 will continue to rotate in the clockwise direction until the right-locking protrusion 342 rides-up against the stationary protrusion 150, which causes the plug deck 300 to again deform and separate slightly from the upper housing 100. This slight separation allows the right-locking protrusion 340 to slip over the stationary protrusion 150 into the maximum clockwise rotation. In this position, the right stop face 352 abuts a portion of the upper housing 100 to prevent further rotation in the clockwise direction, while the right-locking protrusion 340 is locked in place by the stationary protrusion 150. Thus, the plug deck 300 is securely locked in each of the proper use positions. Preferably, each time the one of the left- or right-locking protrusions 340, 342 is forced past the stationary protrusion 150 it makes an audible "click" sound so that the user knows the plug deck 300 has reached a proper use position.

The evaporator may also be provided with various other features, such as one or more of a fan to enhance the diffusion of the active substance into a room, louvers formed in the housing to further enhance the diffusion of the active substance, one or more extra electrical sockets for plugging an additional electrical device through the evaporator, and the appropriate circuitry necessary to provide these features. Each of these features can be provided in a known manner, as disclosed in, for example, the '241 publication, which has been incorporated herein by reference.

The embodiments discussed above are representative of preferred embodiments of my invention and are provided for illustrative purposes only. They are not intended to limit the scope of the invention. Although specific structures, dimensions, components, etc., have been shown and described, such are not limiting. Modifications and variations are contemplated within the scope of my invention, which is intended to be limited only by the scope of the accompanying claims.

INDUSTRIAL APPLICABILITY

My invention provides an electrical evaporator for use with liquid formulations containing a chemical active such as an insecticide, fragrance, or the like. The evaporator includes an improved, ratcheting adjuster for varying the evaporation rate of the liquid formulation. Thus, the concentration of the chemical active dispersed into the surrounding environment can be precisely controlled, depending on a user's preferences.

I claim:

1. An evaporator comprising:
    a bottle containing a substance to be evaporated, and a wick having a lower portion disposed in the substance in said bottle and an upper portion protruding from said bottle;
    a housing adapted to receive said bottle and wick;
    an electrical plug assembly coupled to said housing for supporting the evaporator in a wall outlet;
    a heating device disposed within said housing in electrical communication with said electrical plug assembly; and
    an adjuster disposed in said housing and adapted to adjust a spacing of the wick relative to said heating device, said adjuster including a ratcheting mechanism that retains said adjuster in any one of a plurality of discrete adjustment settings.

2. An evaporator according to claim 1, wherein said bottle and said wick are detachably received by said housing.

3. An evaporator according to claim 1, wherein said ratcheting mechanism comprises a retaining dog that is biased against said housing to retain said adjuster in a desired one of the plurality of discrete adjustment settings.

4. An evaporator according to claim 3, wherein said ratcheting mechanism further comprises a cantilever arm that biases said retaining dog against said housing.

5. An evaporator according to claim 4, wherein said housing includes a serrated adjustment surface against which said retaining dog is biased, the serrated adjustment surface having a plurality of peaks and valleys, each valley corresponding to one of the plurality of discrete adjustment settings.

6. An evaporator according to claim 5, wherein said retaining dog is rigid and said cantilever arm is flexible so as to allow said retaining dog to move up over each of the plurality of peaks and down into each of the plurality of valleys while riding along the serrated adjustment surface of said housing.

7. An evaporator according to claim 5, wherein rotation of said adjuster causes a ratcheting sound and feel as said retaining dog rides along the serrated surface of said housing, whereby the user can sense movement of the adjuster between each of the plurality of discrete adjustment settings by both auditory and tactile perception.

8. An evaporator according to claim 3, wherein said adjuster further comprises a hollow cylindrical portion adapted to receive the upper portion of the wick.

9. An evaporator according to claim 8, wherein said adjuster further comprises a dial portion for rotating said hollow cylindrical portion about an axis of rotation.

10. An evaporator according to claim 9, wherein said dial portion is formed integrally with said hollow cylindrical portion.

11. An evaporator according to claim 8, wherein said hollow cylindrical portion is rotatable through a range of rotation of about 180 degrees.

12. An evaporator according to claim 8, wherein said hollow cylindrical portion defines an opening through which the wick extends, and the center of the opening is offset relative to the axis of rotation of said hollow cylindrical portion.

13. An evaporator according to claim 1, wherein said adjuster further comprises a hollow cylindrical portion adapted to receive the upper portion of the wick, and a dial portion formed integrally with said hollow cylindrical portion for rotating said hollow cylindrical portion about an axis of rotation, and
    wherein said ratcheting mechanism comprises a retaining dog that is biased into contact with a serrated adjustment surface of said housing to retain said adjuster in a desired one of said plurality of adjustment settings, the serrated adjustment surface having a plurality of peaks and valleys, each valley corresponding to one of the plurality of discrete adjustment settings.

14. An evaporator comprising:
    a bottle containing a substance to be evaporated, and a wick having a lower portion disposed in the substance in said bottle and an upper portion protruding from said bottle;
    a housing adapted to receive said bottle and wick;
    a heating device disposed within said housing and adapted to apply heat to the wick; and
    an electrical plug assembly, including a plug deck, coupled to said housing for supporting the evaporator in a wall outlet and supplying power to said heating device, said plug deck being rotatable in order to support the evaporator in an upright position in both horizontal and vertical wall outlets, and said plug deck including a locking mechanism which retains said plug deck in one of a plurality of discrete positions relative to said housing; and an adjuster disposed within said housing and adapted to adjust a spacing of the wick relative to said heating device, said adjuster including a ratcheting mechanism that retains said adjuster in any one of a plurality of discrete adjustment settings.

15. An evaporator according to claim 14, wherein said adjuster further comprises a hollow cylindrical portion adapted to receive an upper portion of the wick, and a dial portion formed integrally with said hollow cylindrical portion for rotating said hollow cylindrical portion about an axis of rotation, and wherein said ratcheting mechanism comprises a retaining dog that is biased into contact with a serrated adjustment surface of said housing to retain said adjuster in a desired one of said plurality of adjustment settings, the serrated adjustment surface having a plurality of peaks and valleys, each valley corresponding to one of the plurality of discrete adjustment settings.

16. An evaporator according to claim 15, wherein said locking mechanism comprises at least one protrusion formed on said housing, that engages at least one protrusion formed on said plug deck to lock said plug deck in one of the plurality of discrete positions, and wherein said plug deck further comprises a left stop face for limiting rotation of said plug deck in the counter-clockwise direction and a right stop face for limiting rotation of said plug deck in the clockwise direction.

17. An electrical evaporator comprising:

a bottle containing a substance to be evaporated, and a wick having a lower portion disposed in the substance in said bottle and an upper portion protruding from said bottle;

a housing adapted to receive said bottle and wick;

an electrical plug assembly coupled to said housing for supporting the evaporator in a wall outlet;

a heating device disposed within said housing in electrical communication with said electrical plug assembly; and an adjuster disposed in said housing for adjusting a spacing of the wick relative to said heating device, said adjuster including a retaining dog that is biased into contact with said housing to retain said adjuster in any one of a plurality of discrete adjustment settings.

18. An evaporator according to claim 17, wherein said retaining dog is biased into contact with a serrated adjustment surface of said housing to retain said adjuster in a desired one of said plurality of adjustment settings, the serrated adjustment surface having a plurality of peaks and valleys, each valley corresponding to one of the plurality of discrete adjustment settings.

19. An evaporator according to claim 18, wherein rotation of said adjuster causes a ratcheting sound and feel as said retaining dog rides along the serrated adjustment surface of said housing, whereby the user can sense movement of the adjuster between each of the plurality of discrete adjustment settings by both auditory and tactile perception.

\* \* \* \* \*